United States Patent
Qu et al.

(10) Patent No.: US 12,352,806 B2
(45) Date of Patent: Jul. 8, 2025

(54) DEVICES AND METHODS FOR SMART SENSOR APPLICATION

(71) Applicant: Analog Devices International Unlimited Company, Limerick (IE)

(72) Inventors: GuangYang Qu, Beijing (CN); Yincai Tony Liu, Beijing (CN); Baotian Hao, Beijing (CN); Hanqing Wang, Beijing (CN); Hengfang Mei, Beijing (CN); Rengui Luo, Beijing (CN); Yimiao Zhao, Beijing (CN); Junbiao Ding, Shanghai (CN)

(73) Assignee: Analog Devices International Unlimited Company, Limerick (IE)

( * ) Notice: Subject to any disclaimer, the term of this patent is extended or adjusted under 35 U.S.C. 154(b) by 180 days.

(21) Appl. No.: 18/132,256

(22) Filed: Apr. 7, 2023

(65) Prior Publication Data

US 2023/0251302 A1    Aug. 10, 2023

Related U.S. Application Data (60) Division of application No. 17/463,103, filed on Aug. 31, 2021, now Pat. No. 11,656,269, which is a (Continued)

(51) Int. Cl.
*G01R 31/28* (2006.01)
*G01N 27/12* (2006.01)
(Continued)

(52) U.S. Cl.
CPC ..... *G01R 31/2829* (2013.01); *G01N 27/4163* (2013.01); *G01N 33/0057* (2013.01);
(Continued)

(58) Field of Classification Search
CPC .... G01R 31/2829; G01R 27/02; G01R 27/16; G01R 35/005; G01R 31/2812;
(Continued)

(56) References Cited

U.S. PATENT DOCUMENTS 3,711,850 A    1/1973   Kelly
4,178,793 A   12/1979   Bremer et al.
(Continued)

FOREIGN PATENT DOCUMENTS

CN        1128091 A       7/1996
CN      101685117 A  *    3/2010
(Continued)

OTHER PUBLICATIONS

"U.S. Appl. No. 15/433,862 Supplemental Amendment Filed Jul. 23, 2019", 7 pgs.
(Continued)

*Primary Examiner* — Jermele M Hollington
*Assistant Examiner* — Robert P Alejnikov, Jr.
(74) *Attorney, Agent, or Firm* — Schwegman Lundberg & Woessner, P.A.

(57) ABSTRACT

An apparatus comprises an integrated circuit that includes an input to receive an electrical input signal from an electronic sensor, wherein the input signal includes a direct current (DC) offset and a varying signal component; a digital-to-analog converter (DAC) circuit configured to subtract the DC offset from the input signal; a programmable gain amplifier (PGA) operatively coupled to the DAC circuit, wherein the PGA circuit is configured to apply signal gain to the varying signal component of the input signal; and a measurement circuit configured to generate a measure of the varying signal component.

20 Claims, 7 Drawing Sheets

Related U.S. Application Data division of application No. 16/584,212, filed on Sep. 26, 2019, now Pat. No. 11,119,143, which is a division of application No. 15/433,862, filed on Feb. 15, 2017, now Pat. No. 10,466,296, which is a continuation of application No. PCT/CN2017/070608, filed on Jan. 9, 2017.

(51) Int. Cl.
*G01N 27/416* (2006.01)
*G01N 33/00* (2006.01)
*G01R 27/02* (2006.01)
*G01R 27/16* (2006.01)
*G01R 35/00* (2006.01)

(52) U.S. Cl.
CPC .............. *G01R 27/02* (2013.01); *G01R 27/16* (2013.01); *G01R 35/005* (2013.01); *G01N 27/122* (2013.01)

(58) Field of Classification Search
CPC ............... G01R 35/00; G01N 27/4163; G01N 33/0057; G01N 27/122; G01N 27/406; G01N 27/417
USPC ...................................................... 324/750.3
See application file for complete search history.

(56) References Cited

U.S. PATENT DOCUMENTS

| | | | |
|---|---|---|---|
| 4,196,475 A | 4/1980 | Hall | |
| 4,470,020 A | 9/1984 | Mohr | |
| 4,543,560 A | 9/1985 | Holloway | |
| 4,847,783 A | 7/1989 | Grace et al. | |
| 4,857,827 A | 8/1989 | Zoltan | |
| 4,970,470 A | 11/1990 | Gosser | |
| 5,123,732 A | 6/1992 | Gross et al. | |
| 5,495,245 A | 2/1996 | Ashe | |
| 5,557,267 A | 9/1996 | Poduje et al. | |
| 5,621,669 A | 4/1997 | Bjornsson | |
| 5,980,728 A | 11/1999 | Farber et al. | |
| 6,050,989 A | 4/2000 | Fox et al. | |
| 6,090,123 A | 7/2000 | Culp et al. | |
| 6,307,497 B1 | 10/2001 | Leung et al. | |
| 6,313,779 B1 | 11/2001 | Leung et al. | |
| 6,414,616 B1 | 7/2002 | Dempsey | |
| 6,520,969 B2 | 2/2003 | Lambrecht et al. | |
| 6,707,404 B1 | 3/2004 | Yilmaz | |
| 6,736,829 B1 | 5/2004 | Li et al. | |
| 6,752,816 B2 | 6/2004 | Culp et al. | |
| 6,786,897 B2 | 9/2004 | McIe et al. | |
| 6,798,282 B1 | 9/2004 | Broekaert et al. | |
| 6,885,328 B1 | 4/2005 | Kao et al. | |
| 6,917,183 B2 | 7/2005 | Barlev et al. | |
| 6,958,071 B2 | 10/2005 | Carusillo et al. | |
| 6,960,894 B2 | 11/2005 | Carusillo et al. | |
| 6,975,103 B1 | 12/2005 | Blom | |
| 7,041,120 B2 | 5/2006 | Li et al. | |
| 7,204,638 B2 | 4/2007 | Hsu | |
| 7,649,363 B2 | 1/2010 | Lemson | |
| 7,999,232 B2 | 8/2011 | Wilson et al. | |
| 8,054,085 B2 | 11/2011 | Johansen et al. | |
| 8,284,090 B2 | 10/2012 | Maurino | |
| 8,310,277 B2 | 11/2012 | Su et al. | |
| 8,319,507 B2 | 11/2012 | Gautama | |
| 8,502,567 B2 | 8/2013 | Lawas | |
| 8,872,689 B2 | 10/2014 | Mayer et al. | |
| 8,912,939 B2 | 12/2014 | Dempsey | |
| 8,981,798 B2 | 3/2015 | Scuderi | |
| 9,124,296 B2 | 9/2015 | Dempsey | |
| 9,213,016 B1 | 12/2015 | Stetter et al. | |
| 9,296,298 B2 | 3/2016 | Williams et al. | |
| 9,322,850 B2 | 4/2016 | Wood et al. | |
| 10,466,296 B2 | 11/2019 | Qu et al. | |
| 11,119,143 B2 | 9/2021 | Qu et al. | |
| 11,656,269 B2 | 5/2023 | Qu et al. | |
| 11,683,026 B1* | 6/2023 | Chakraborty | H03K 5/01 327/527 |
| 2002/0153901 A1 | 10/2002 | Davis et al. | |
| 2003/0127323 A1 | 7/2003 | Bolz | |
| 2004/0051122 A1* | 3/2004 | Takahashi | H03D 7/1408 257/E23.144 |
| 2004/0099041 A1 | 5/2004 | Hattori | |
| 2005/0192765 A1 | 9/2005 | Slothers et al. | |
| 2005/0230248 A1 | 10/2005 | Kawase et al. | |
| 2006/0011476 A1 | 1/2006 | Hada et al. | |
| 2008/0196480 A1 | 8/2008 | Kawase et al. | |
| 2009/0184754 A1 | 7/2009 | Chen | |
| 2009/0288469 A1 | 11/2009 | Ding | |
| 2013/0015843 A1 | 1/2013 | Doogue et al. | |
| 2014/0145737 A1 | 5/2014 | Lacombe et al. | |
| 2014/0191773 A1 | 7/2014 | Saijoh et al. | |
| 2014/0290337 A1 | 10/2014 | Higuchi et al. | |
| 2015/0078560 A1 | 3/2015 | Ilango et al. | |
| 2015/0185050 A1 | 7/2015 | Stothers et al. | |
| 2015/0362457 A1 | 12/2015 | Watanabe | |
| 2018/0196101 A1 | 7/2018 | Qu et al. | |
| 2019/0170687 A1 | 6/2019 | Heien et al. | |
| 2020/0033398 A1 | 1/2020 | Qu et al. | |
| 2021/0405110 A1 | 12/2021 | Qu et al. | |

FOREIGN PATENT DOCUMENTS

| | | | |
|---|---|---|---|
| CN | 101796624 A | 8/2010 | |
| CN | 101981459 A | 2/2011 | |
| CN | 102193018 A | 9/2011 | |
| CN | 103267891 B | 6/2015 | |
| CN | 204925248 | 12/2015 | |
| CN | 104897964 | 3/2018 | |
| CN | 113376507 A | 9/2021 | |
| CN | 109791178 B | 10/2021 | |
| CN | 113970693 A | 1/2022 | |
| DE | 9312517 U1 | 10/1993 | |
| EP | 0053786 A1 | 6/1982 | |
| EP | 0271849 A2 | 6/1988 | |
| EP | 0496147 | 7/1992 | |
| EP | 0802420 A2 | 10/1997 | |
| EP | 2976650 | 1/2016 | |
| GB | 2411481 A | 8/2005 | |
| JP | H09203667 A | 8/1997 | |
| JP | 2000329730 A | 11/2000 | |
| JP | 2002155796 A | 5/2002 | |
| JP | 2002213991 A | 7/2002 | |
| JP | 2003066077 A | 3/2003 | |
| JP | 2004177178 A | 6/2004 | |
| JP | 2004279293 A | 10/2004 | |
| JP | 2007005945 A * | 1/2007 | |
| JP | 2012137298 A | 7/2012 | |
| JP | 2015121466 A | 7/2015 | |
| JP | 2016061625 A | 4/2016 | |
| JP | 7390976 B | 11/2023 | |
| WO | WO-0108294 A1 * | 2/2001 | ......... G01N 27/4163 |
| WO | 2005085883 | 9/2005 | |
| WO | WO-2012136923 A1 | 10/2012 | |
| WO | WO-2018127793 A1 | 7/2018 | |

OTHER PUBLICATIONS

"U.S. Appl. No. 15/433,862, Notice of Allowance mailed May 30, 2019", 11 pgs.

"U.S. Appl. No. 15/433,862, Notice of Allowance mailed Aug. 21, 2019", 10 pgs.

"U.S. Appl. No. 15/433,862, Response filed May 3, 2019 to Restriction Requirement mailed Mar. 7, 2019", 5 pgs.

"U.S. Appl. No. 15/433,862, Restriction Requirement mailed Mar. 7, 2019", 10 pgs.

"U.S. Appl. No. 16/584,212, Notice of Allowance mailed May 13, 2021", 20 pgs.

"U.S. Appl. No. 16/584,212, Preliminary Amendment filed Oct. 17, 2019", 7 pgs.

(56) References Cited

OTHER PUBLICATIONS

"U.S. Appl. No. 17/463,103, Non Final Office Action mailed Sep. 28, 2022", 16 pgs.
"U.S. Appl. No. 17/463,103, Notice of Allowance mailed Jan. 20, 2023", 11 pgs.
"U.S. Appl. No. 17/463,103, Preliminary Amendment filed Sep. 20, 2021", 6 pgs.
"U.S. Appl. No. 17/463,103, Response filed Dec. 21, 2022 to Non Final Office Action mailed Sep. 28, 2022", 8 pgs.
"Chinese Application Serial No. 202111179855.1, Voluntary Amendment filed May 13, 2022", w/ English Claims, 10 pgs.
"Chinese Application Serial No. 201880003803.9, Office Action mailed Jun. 2, 2021", w/ English Translation, 10 pgs.
"Chinese Application Serial No. 201880003803.9, Office Action mailed Sep. 22, 2020", w/ English Translation, 18 pgs.
"Chinese Application Serial No. 201880003803.9, Response filed Jun. 21, 2021 to Office Action mailed Jun. 2, 2021", w/ English claims, 9 pgs.
"Chinese Office Action Serial No. 201880003803.9, Response filed Feb. 5, 2021 to Office Action mailed Sep. 22, 2020", w/ English Claims, 11 pgs.
"German Application Serial No. 112018000004.4, Office Action mailed Mar. 11, 2022", w/ English Machine Translation, 16 pgs.
"German Application Serial No. 112018000004.4, Response filed Jul. 12, 2022 to Office Action mailed Mar. 11, 2022", w/ English Machine Translation, 100 pgs.
"International Application Serial No. PCT/IB2018/000278, International Search Report mailed Jun. 21, 2018", 9 pgs.
"International Application Serial No. PCT/IB2018/000278, Written Opinion mailed Jun. 21, 2018", 11 pgs.
"Japanese Application Serial No. 2018-569191, Office Action mailed Feb. 25, 2020", w/ English translation, 9 pgs.
"Japanese Application Serial No. 2020-090592, Examiners Decision of Final Refusal mailed Apr. 4, 2022", w/ English translation, 6 pgs.
"Japanese Application Serial No. 2020-090592, Notification of Reasons for Refusal mailed Aug. 30, 2021", w/ English Translation, 15 pgs.
"Japanese Application Serial No. 2020-090592, Preliminary Examination Report mailed Oct. 17, 2022", w/o English Translation, 2 pgs.
"Japanese Application Serial No. 2020-090592, Response filed Jan. 17, 2023 Preliminary Examination Report mailed Oct. 17, 2022", 6 pgs.
"Japanese Application Serial No. 2020-090592, Response filed Jul. 22, 2022 to Examiners Decision of Final Refusal mailed Apr. 4, 2022", w/ English Claims, 9 pgs.
"Japanese Application Serial No. 2020-090592, Response filed Nov. 30, 2021 to Notification of Reasons for Refusal mailed Aug. 30, 2021", w/ English Claims, 9 pgs.
Ahmed, A Helmy, et al., "A Self-Sustained CMOS Microwave Chemical Sensor Using a Frequency Synthesizer", IEEE Journal of Solid State Circuits, vol. 47, No. 10, (Oct. 2012), 2467-2483.
Igarashi, Brian, et al., "An impedance-measurement setup optimized for measuring relaxations of glass-forming liquids", Review of Scientific Instruments, vol. 79, Issue 4, (2008), 1 pg.
"Japanese Application Serial No. 2020-090592, Notification of Reasons for Rejection mailed Jun. 26, 2023", w/ English Translation, 7 pgs.
"Chinese Application Serial No. 202111179855.1, Office Action mailed Jul. 27, 2023", 9 pgs.
"Japanese Application Serial No. 2020-090592, Response filed Aug. 17, 2023 to Notification of Reasons for Rejection mailed Jun. 26, 2023", w/ English claims, 5 pgs.
"Chinese Application Serial No. 202110600184.5, Office Action mailed Feb. 1, 2024", w/ English Translation, 12 pgs.
"Chinese Application Serial No. 202110600184.5, Office Action mailed Aug. 31, 2024", w/ English translation, 7 pgs.
"Chinese Application Serial No. 202110600184.5, Response filed Jun. 3, 2024 to Office Action mailed Feb. 1, 2024", W/English Claims, 11 pgs.
"Chinese Application Serial No. 202110600184.5, Response filed Oct. 31, 2024 to Office Action mailed Aug. 31, 2024", W/English Claims, 11 pgs.
"Chinese Application Serial No. 202111179855.1, Decision of Rejection mailed Jun. 28, 2024", w/ English translation, 5 pgs.
"Chinese Application Serial No. 202111179855.1, Office Action mailed Feb. 20, 2024", w/o English Translation, 6 pgs.
"Chinese Application Serial No. 202111179855.1, Response filed Apr. 16, 2024 to Office Action mailed Feb. 20, 2024", W/English Claims, 17 pgs.
"Chinese Application Serial No. 202111179855.1, Response filed Sep. 29, 2024 to Decision of Rejection mailed Jun. 28, 2024", w/ current English claims, 15 pgs.
"Chinese Application Serial No. 202111179855.1, Response Filed Dec. 7, 2023 to Office Action mailed Jul. 27, 2023", w/ Englsih Claims, 18 pgs.

\* cited by examiner

FIG. 10

DEVICES AND METHODS FOR SMART SENSOR APPLICATION

CLAIM OF PRIORITY

This application is a divisional of U.S. patent application Ser. No. 17/463,103, filed on Aug. 31, 2023, which is a divisional of U.S. patent application Ser. No. 16/584,212, filed on Sep. 26, 2019, which is a divisional of U.S. patent application Ser. No. 15/433,862, filed on Feb. 15, 2017, which is a continuation of CN PCT Application No. PCT/CN2017/070608, filed on Jan. 9, 2017, which are hereby incorporated by reference in its entireties.

FIELD OF THE DISCLOSURE

This document relates generally to interface circuits for electronic sensors. Some embodiments relate to test circuits for electronic sensors.

BACKGROUND

Smart sensors are electronic circuits that measure some aspect of their environment and trigger computing resources to perform predefined functions in response to the measurements. Smart sensors are useful in application such as implementing an internet of things (IoT). Sometimes the output of a smart sensor needs to be tailored to the monitoring electronics operatively coupled to the smart sensors to acquire information for the computing resources. The present inventors have recognized a need for improved interface circuits for smart sensor circuits.

SUMMARY OF THE DISCLOSURE

This document relates generally to interface circuits for electronic sensors.

Aspect 1 of the present disclosure includes subject matter (such as a test circuit for an electronic sensor) comprising a load resistance connectable in series with the electronic sensor to form a series resistance of the load resistance and the internal impedance of the electronic sensor; an excitation circuit configured to apply a predetermined voltage to a circuit element; and a measurement circuit configured to: initiate applying the predetermined voltage to the series resistance and determining the series resistance; initiate applying the predetermined voltage to the load resistance and determining the load resistance; and calculate the internal impedance of the sensor using the determined series resistance and the load resistance, and provide the calculated internal impedance to a user or process.

In aspect 2, the subject matter of aspect 1 optionally includes an excitation circuit configured to apply a specified electrical signal having a signal amplitude less than twenty millivolts (20 mV) to the series resistance, and the internal impedance of the electronic sensor is less than ten ohms (10Ω).

In aspect 3, the subject matter of one or both of Aspects 1 and 2 optionally include the electronic sensor being an electro-chemical sensor.

Aspect 4 includes subject matter (such as an integrated circuit), or can optionally be combined with the any combination of Aspects 1-3 to include such subject matter, comprising an excitation circuit configured to apply excitation signals to a sensor circuit, wherein the excitation circuit includes a configurable first circuit gain stage and a configurable second circuit gain stage, wherein in a first gain mode the excitation circuit generates a first excitation signal from a test signal using a first signal gain applied by the first circuit gain stage and a second signal gain applied by the second circuit gain stage, and in a second gain mode the excitation circuit generates a second excitation signal from the test signal using a third signal gain applied by the first circuit gain stage and a fourth signal gain applied by the second circuit gain stage; and a measurement circuit configured to selectively initiate application of the first excitation signal or the second excitation signal to the electronic sensor and calculate the internal impedance of the sensor In aspect 5, the subject matter of Aspect 4 optionally includes a measurement circuit configured to initiate application of the first excitation signal to the electronic sensor when the internal impedance of the sensor has a first internal impedance range and initiate application of the second excitation signal to the electronic sensor when the internal impedance of the sensor has a second internal impedance range, wherein the first internal impedance is greater than the second internal impedance range.

In aspect 6, the subject matter of one or both of Aspects 4 and 5 optionally includes the signal gain of the second gain circuit stage being one in the first gain mode, and less than one and greater than zero in the second gain mode.

In aspect 7, the subject matter of one or any combination of Aspects 4-6 optionally includes the signal gain of the first gain circuit stage being greater than one in the first gain mode, and less than one and greater than zero in the second gain mode.

In aspect 8, the subject matter of one or any combination of Aspects 4-7 optionally includes a digital-to-analog converter (DAC) circuit configured to generate the test signal.

Aspect 9 includes subject matter (such as a test circuit), or can optionally be combined with one or any combination of Aspects 1-8 to include such subject matter, comprising: an adjustable bridge resistance and a calibration resistance for coupling to an electronic sensor; an excitation circuit configured to apply an excitation signal to the electronic sensor, bridge resistance and calibration resistance; and a measurement circuit configured to: apply a first excitation signal to a calibration resistance and measure a calibration current; apply the first excitation signal to a first bridge resistance and measure a first bridge current; apply a second excitation signal to the first bridge resistance and measure a second bridge current; apply the second excitation signal to the sensor and measure a sensor current; and calculate the internal impedance of the sensor using the calibration resistance, the calibration current, the first bridge current, the second bridge current, and the sensor current.

In aspect 10, the subject matter of Example 9 optionally includes a multiplexer circuit configured to selectively apply an excitation signal to the calibration resistance, the adjustable bridge resistance, or the sensor.

In aspect 11, the subject matter of one or both of Aspects 9 and 10 optionally includes a multiplexer circuit configured to apply an excitation signal to the calibration resistance, and the measurement circuit is configured to calculate the calibration resistance using the excitation signal.

In aspect 12, the subject matter of one or any combination of Aspects 9-11 optionally includes a measurement circuit configured to set the bridge resistance to a coarse bridge resistance value prior to the applying the excitation signal to the bridge resistance.

In aspect 13, the subject matter of one or any combination of Aspects 9-12 optionally includes a measurement circuit configured to: apply a third excitation signal to the first bridge resistance and measure a third bridge current, apply the third excitation signal to a second bridge resistance and measure a fourth bridge current, and calculate the internal impedance of the sensor using the calibration resistance, the calibration current, the first bridge current, the second bridge current, the third bridge current, the fourth bridge current, and the sensor current.

In aspect 14, the subject matter of one or any combination of Aspects 9-13 optionally includes the electronic sensor being an electrochemical sensor and the resistance of the electronic sensor is representative of the remaining useful life of the electrochemical sensor.

Aspect 15 includes subject matter (such as an apparatus), or can optionally be combined with the subject matter of one or any combination of Examples 1-14 to include such subject matter comprising an integrated circuit. The integrated circuit includes an input to receive an electrical signal from an electronic sensor, wherein the electrical signal includes a direct current (DC) offset and a varying signal component; a digital-to-analog converter (DAC) circuit configured to subtract the DC offset from the input signal; a programmable gain amplifier (PGA) operatively coupled to the DAC circuit, wherein the PGA circuit is configured to apply signal gain to the varying signal component of the input signal; and a measurement circuit configured to generate a measure of the varying signal component.

In aspect 16, the subject matter of Aspect 15 optionally includes a measurement circuit that includes an analog-to-digital converter (ADC) circuit configured to generate a measure of the varying signal component.

In aspect 17, the subject matter of one or both of Aspects 15 and 16 optionally includes a measurement circuit including a fast Fourier transform (FFT) circuit configured to measure a frequency response of the varying signal component.

In aspect 18, the subject matter of one or any combination of Aspects 15-17 optionally includes an electronic sensor operatively coupled to the integrated circuit, wherein the electronic sensor is a resistive electronic sensor.

In aspect 19, the subject matter of one or any combination of Aspects 15-18 optionally includes an electronic sensor being a gas sensor and the electrical signal from the electronic sensor is proportional to an amount of gas in an atmosphere.

In aspect 20, the subject matter of one or any combination of Aspects 15-20 optionally includes a detection circuit, wherein the electronic sensor is an oxygen sensor and the detection circuit is configured to generate an indication of a lower explosive limit according to the measure of the varying signal component.

Aspect 21 can include, or can optionally be combined with any portion or combination of any portions of any one or more of Examples 1-20 to include, subject matter that can include means for performing any one or more of the functions of Aspects 1-20, or a machine-readable medium including instructions that, when performed by a machine, cause the machine to perform any one or more of the functions of Aspects 1-20.

These non-limiting aspects can be combined in any permutation or combination. This section is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Some smart sensor circuits can include electro-chemical sensors to monitor an amount or concentration of gas. System demands on the sensors often require a sensor circuit to have low power consumption and exhibit low noise to reduce errors. To maximize longevity and minimize servicing, it is desired for the monitoring circuits to also have low power consumption. This can provide challenges in designing circuits to monitor different types of smart sensor circuits. For instance, it may be necessary to measure the impedance of a sensor circuit for diagnostic purposes, but smart sensors can have a wide range of internal impedances. Some sensor may have an internal resistance greater than ten kilo-ohms (10 k$\Omega$) while other sensors may have a low internal resistance (e.g., 1$\Omega$). A sensor with a low internal impedance typically requires a higher voltage measurement signal to provide an adequate signal to noise ratio (SNR). However, applying a higher voltage measurement signal to a low impedance can lead to high current consumption by the measurement circuit and sometimes the sensor circuit cannot tolerate the currents associated with the higher measurement.

Figure 1A:
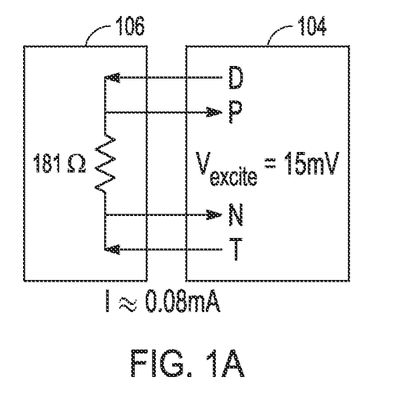
FIGS. 1A and 1B are block diagrams representing a test circuit and sensor circuit.
Figure 1B:
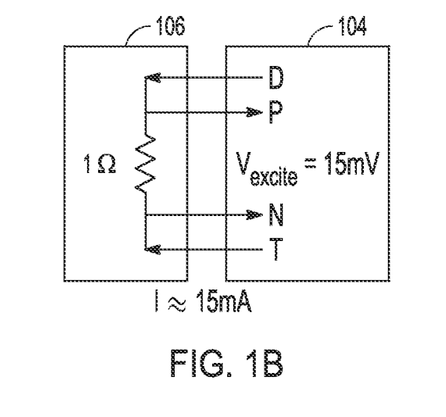

FIGS. 1A and 1B are block diagrams of a test circuit 104 and sensor circuit 106. The test circuit 104 may be included on an integrated circuit. To measure the internal impedance of the sensor circuit, an excitation signal is applied between a drive or "D" connection and a transimpedance amplifier (TIA) or "T" connection. The "P" and "N" connections are sensing nodes for operation of the sensor. To determine the internal impedance of the sensor circuit, the test circuit applies an excitation signal to the sensor circuit using the D and T connections. In FIG. 1A the excitation signal has a magnitude of fifteen millivolts (15 mV), and the sensor circuit 106 has an internal impedance of 18152. Applying the excitation signal results in a current through the sensor of 0.08 milliamps (0.08 mA). The test circuit can determine the internal resistance of the sensor circuit using Ohm's Law. The test circuit can provide the determined internal impedance to a user (e.g., by presenting the value of on a display) or to a process (e.g., a process that stores the value in memory or a process that uses the determined impedance to take some action).

In FIG. 1B, the sensor circuit 106 has an internal resistance of 1Ω, but it may be desired to measure the sensor with the same 15 mV excitation signal. However, a straightforward application of the excitation signal results in a current of 15 mA. This current may cause problems for multiple reasons. For instance, the current may be too large for a desired power consumption, or the sensor circuit may not be able to tolerate a current of that magnitude. Also, trying to accommodate a current of 0.08 mA and a current of 15 mA may cause accuracy issues in measurements made by the monitoring circuits. Reducing the excitation voltage may significantly reduce the SNR.

Figure 2A:
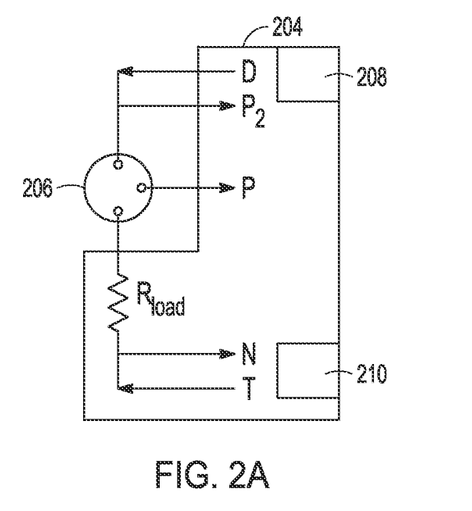
FIGS. 2A and 2B are block diagrams representing another test circuit 204 electrically coupled to a sensor circuit.
Figure 2B:
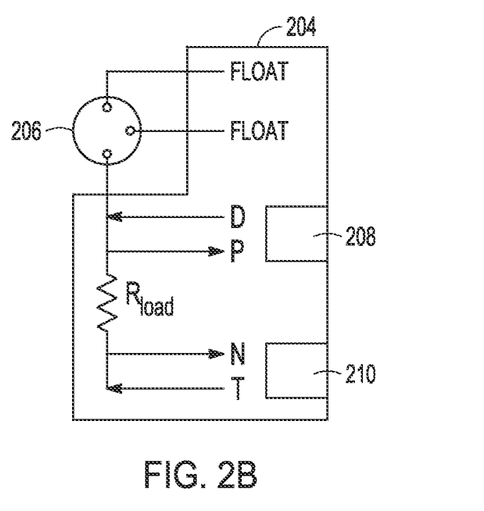

FIGS. 2A and 2B are block diagrams of further examples of a test circuit 204 electrically coupled to a sensor circuit 206. The test circuit can be used to determine internal impedances of sensor circuits of about 200Ω and also sensor circuits with internal impedances less than 105Ω. The test circuit includes a load resistance $R_{load}$, an excitation circuit 208, and a measurement circuit 210. The load resistance may have a resistance value of 100Ω (in certain embodiments the load resistance has a resistance value of about 200Ω). The measurement circuit can include logic circuits to perform the described functions. In variations, the measurement circuit includes a processor such as a microprocessor. In FIG. 2A, when a sensor circuit with a low impedance is to be monitored, the measurement circuit 210 connects the load resistance in series with the internal impedance of the sensor circuit to form a series resistance. The excitation circuit 208 applies an excitation signal having a predetermined voltage to the series resistance. In variations the predetermined voltage is less than or equal to 20 mV. The measurement circuit determines the series resistance using the resulting current and predetermined voltage. In FIG. 2B, the test circuit then applies the excitation signal to just the load resistance. The excitation signal determines the load resistance using the resulting current and predetermined voltage. The test circuit determines the internal impedance of the sensor circuit by subtracting the load resistance from the series resistance.

Adding in the load resistance results in an internal impedance that is comparable between the two types of sensors. This improves the accuracy in the values of impedance determined by the test circuit. In some examples, the measurement circuit calibrates the predetermined voltage of the excitation signal. A calibration resistor of a predetermined resistor can be electrically connected to outputs of the test circuit and the test circuit can adjust the excitation signal until a specified current is measured corresponding to the predetermined voltage of the excitation signal.

Figure 3:
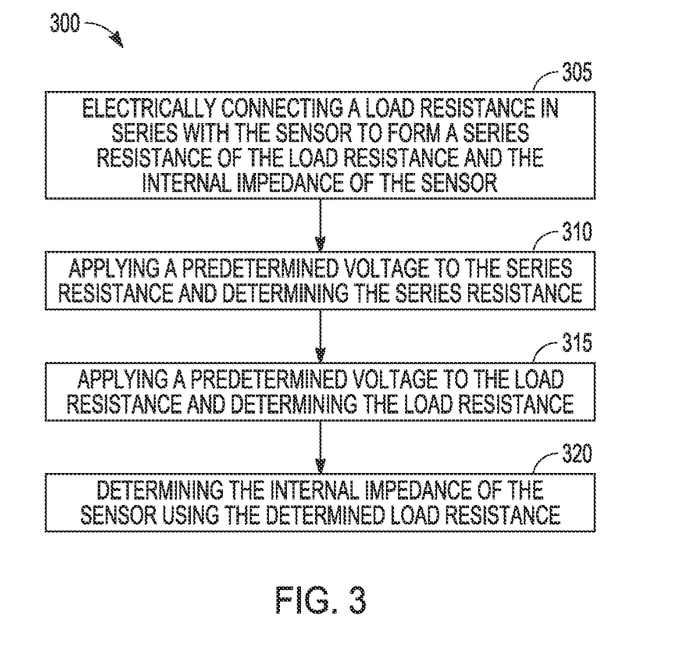
FIG. 3 is a flow diagram of an example of a method of controlling a test circuit to measure an internal impedance of an electronic sensor.

FIG. 3 is a flow diagram of an example of a method 300 of controlling a test circuit to measure an internal impedance of an electronic sensor. At 305, a load resistance is electrically connected in series with the sensor to form a series resistance of the load resistance and the internal impedance of the sensor. At 310, an excitation signal with a predetermined voltage is applied to the series resistance and determining the series resistance is determined (e.g., by Ohm's Law). At 315, the predetermined voltage is applied to the load resistance and the load resistance is determined. At 320, the internal impedance of the sensor is determined using the determined load resistance and series resistance. A value of the internal impedance is provided to a user or process. The approach can be used for other ranges of internal impedance. For example, the test circuit can be used to measure sensor internal impedances of about 1 kΩ to 1Ω.

Figure 4:
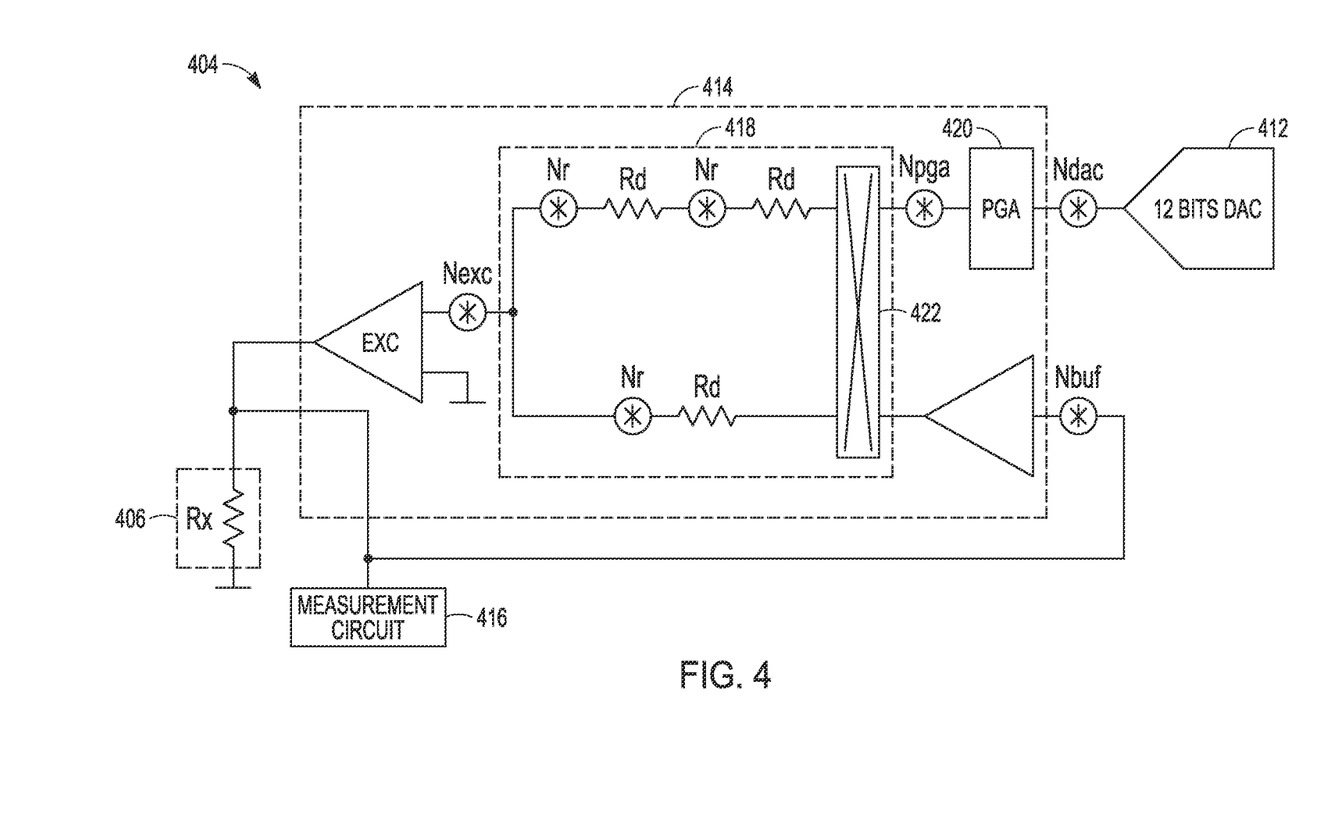
FIG. 4 is circuit diagram of portions of another example of a test circuit electrically coupled to a sensor circuit.

FIG. 4 is circuit diagram of portions of an example of a test circuit 404 electrically coupled to a resistor (Rx) representing the internal impedance of a sensor circuit 406. The test circuit 404 may be included on an integrated circuit. The test circuit 404 includes a digital to analog converter (DAC) circuit 412, an excitation circuit 414 and a measurement circuit 416. To measure the internal impedance, a test signal is generated using a digital to analog converter DAC circuit 412. Using excitation operational amplifier 424, the excitation circuit 414 applies an excitation circuit generated using the test signal to the sensor circuit. A monitoring signal resulting from the excitation is used by the measurement circuit 416 to determine the internal impedance. For instance, an excitation signal of a predetermined voltage can be applied to the sensor circuit and the resulting current signal can be used to determine the internal impedance. The DAC circuit 412 allows excitation signals of different frequency and magnitude to be generated, such as by controlling the DAC circuit 412 with a processor or other control circuit (e.g., a waveform generator).

When the internal impedance to be measured is low, the voltage of the excitation signal may need to be reduced to limit the current through the sensor and limit the power consumption of the test. A challenge with measuring internal impedances for different types of sensors with very different internal impedances is that circuit noise can become significant as the voltage of the excitation signal is reduced.

The excitation circuit 414 includes a configurable first circuit gain stage 420 and a configurable second circuit gain stage 418. The first circuit gain stage 420 includes a programmable gain amplifier (PGA). The second circuit gain stage includes resistors Rd and cross coupled switch circuit 422. The gain of the first circuit stage is configurable by changing the programmable gain and the gain of the second circuit gain stage 418 is configurable by changing the state of the cross coupled switch circuit 422. The combined signal gain of the excitation circuit 414 is configured by the measurement circuit (e.g., using a control circuit) according to whether the internal impedance of the sensor circuit to be measured is in a higher impedance range or lower impedance range. A higher signal gain is provided when the internal impedance is in the higher impedance range.

When the sensor circuit has a value of internal impedance in the higher range, the excitation circuit 414 is configured in a first gain mode. The excitation circuit generates a first excitation signal from the DAC circuit test signal using a first signal gain applied by the first circuit gain stage and a second signal gain applied by the second circuit gain stage. In an example not intended to be limiting, the gain of the first circuit gain stage 420 is 1 and the gain of the second circuit gain stage 418 is two to provide an overall signal gain of two to the test signal in the first gain mode.

When the sensor circuit has a value of internal impedance in the lower range, the excitation circuit 414 is configured in a second gain mode. The excitation circuit generates a second excitation signal from the DAC circuit test signal using a third signal gain applied by the first circuit gain stage and a fourth signal gain applied by the second circuit gain stage. The gains in the second gain mode can be gain values between zero and one. In an example, the gain of the first circuit gain stage 420 is one-tenth (1/10) and the gain of the second circuit gain stage 418 is one-half (1/2) to provide an overall signal gain of one-twentieth (1/20) to the test signal in the second gain mode. The values of signal gain provided by the second gain mode can be changed by changing the resistance values. In certain examples, the second gain stage provides a gain of four or five in the first gain mode and one-fourth (¼) or one-fifth (⅕) in the second gain mode. The measurement circuit 416 selectively initiates application of the first excitation signal or the second excitation signal to the electronic sensor and calculate the internal impedance of the sensor. The small signal gain when the internal impedance is in the lower range reduces circuit noise of the PGA and excitation operational amplifier 424. This improves accuracy in the internal impedance measurement in the lower range.

Figure 5:
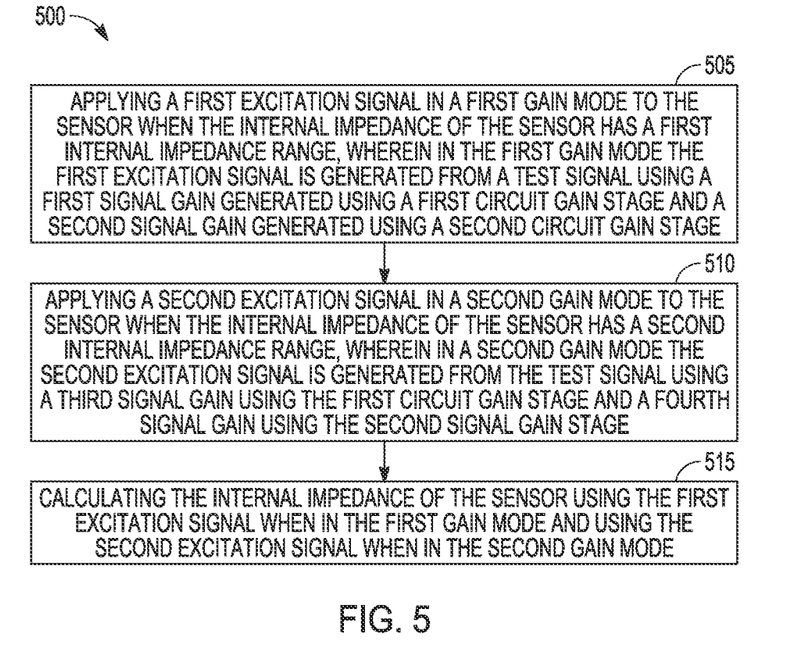
FIG. 5 is a flow diagram of another example of a method of controlling a test circuit to measure an internal impedance of an electronic sensor.

FIG. 5 is a flow diagram of an example of a method 500 of controlling a test circuit to measure an internal impedance of an electronic sensor. At 505, a first excitation signal in a first gain mode is applied to the sensor when the internal impedance of the sensor has a first internal impedance range. In the first gain mode, the first excitation signal is generated from a test signal using a first signal gain generated using a first circuit gain stage and a second signal gain generated using a second circuit gain stage.

At 510, a second excitation signal in a second gain mode is applied to the sensor when the internal impedance of the sensor has a second internal impedance range. In some examples, the values of impedance in the second impedance range are lower than the value of impedance in the first impedance range. In the second gain mode, the second excitation signal is generated from the test signal using a third signal gain using the first circuit gain stage and a fourth signal gain using the second signal gain stage.

At 515, the internal impedance of the sensor is calculated using the first excitation signal when in the first gain mode and using the second excitation signal when in the second gain mode. The calculated internal impedance can be provided to a user or process. The internal impedance range of the sensor circuit and consequently which signal gain to use in measuring the sensor circuit may be known ahead of time (e.g., by the type of sensor) and programmed by a user. In other examples, the measurement circuit can determine which signal gain to apply to the excitation circuit. In some examples, the sensor circuit includes an identifier (e.g., a machine-readable type code) read by the test circuit. In some examples, an excitation signal of a predetermined voltage is applied to the sensor circuit to determine a coarse impedance measurement to determine the internal impedance range of the sensor circuit and the signal gain is set accordingly.

Figure 6:
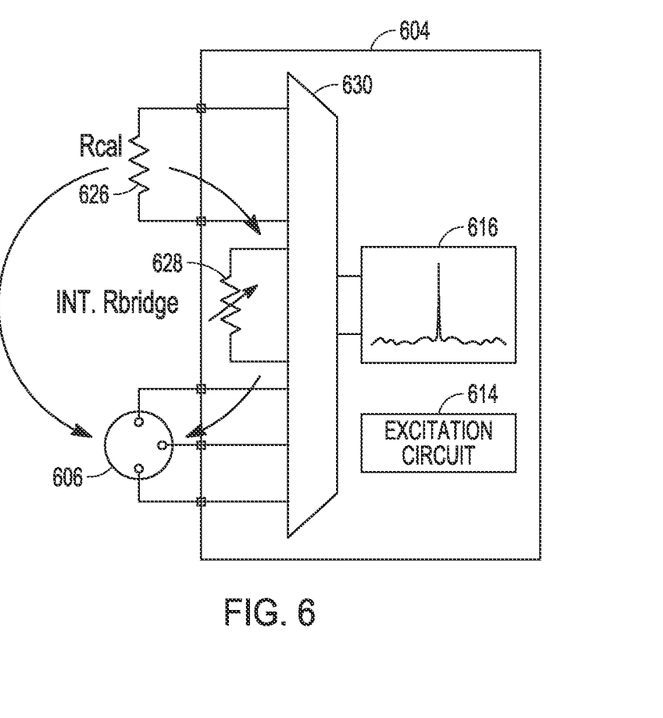
FIG. 6 is circuit diagram of portions of another example of a test circuit electrically coupled to a sensor circuit.

FIG. 6 is circuit diagram of portions of another example of a test circuit 604 electrically coupled to a sensor circuit 606. The test circuit can be included in an integrated circuit. In certain examples, the sensor circuit is included in the same integrated circuit and the test circuit. The electronic sensor can be an electrochemical sensor or a gas sensor. The impedance of the electronic sensor may change as the sensor is used and measuring the impedance of sensor can be useful to estimate the remaining useful life of the sensor. Determining when the sensor is near the end of its useful life may be more important if the sensor is used to sense a toxic substance or gas.

The test circuit 604 includes an excitation circuit 614 and a measurement circuit 616. The excitation circuit provides an excitation signal for measuring impedance. The measurement circuit can include logic circuitry to perform the functions described and may include control circuitry to initiate the measurements and calculations. To determine an unknown impedance of a sensor circuit Rx, an excitation signal Vexc can be applied to the sensor circuit and the sensor current Ix can be measured, where Ix=Vexc/Rx. The same excitation signal Vexc is applied to a known calibration resistance 626 (Rcal) and the calibration current Ical is measured, where Ical=Vexc/Rcal. Because Vexc is the same in both measurements, the unknown impedance of the sensor can be determined as Rx=Rcal(Ical/Ix).

This measurement approach works well if the value of Rx is the same order of magnitude as Rcal. However, the approach works less well if the sensor impedance is too different from Rcal. For instance, if Rcal is about 200Ω and Vexc is 1V, then Iexc is about five milliamps (5 mA). If Rx is one megaohm (1 MΩ), then the Ix is about one microamp (1 μA). These values of current are too different for the measurement circuitry to provide the desired accuracy. Adding gain to the signal for measurement may also add gain to the signal error, which will increase error in the measurement of the signal.

The test circuit 604 of FIG. 6 includes an adjustable bridge resistance 628 in addition to the calibration resistance. The value of the bridge resistance is adjusted to be between the resistance value of Rcal and the value of the sensor impedance. The bridge resistance can be an inexpensive resistance circuit and the resistance may not be known to the desired accuracy. The test circuit 604 can include a multiplexer circuit that can be used to selectively apply the excitation signal to the calibration resistance, the adjustable bridge resistance, or the sensor circuit 606.

A first predetermined excitation signal can be applied to Rcal and the bridge resistance Rb, and a second predetermined excitation signal can be applied to the bridge resistance Rb and the sensor circuit Rx. Different signal gain can be applied to the separate excitation signals and the measured currents can be used to determine the impedance of the electronic sensor.

For instance, the measurement circuit 616 may apply a first excitation signal $Vexc_1$ to the calibration resistance Rcal and measure a calibration current Ical. The first excitation signal is applied to the bridge resistance Rb and a first bridge current $Ib_1$ can be measured. The measurement circuit 616 applies a second excitation signal $Vexc_2$ to the bridge resistance value and a second bridge current $Ib_2$ can be measured. The second excitation signal is applied to the sensor and a sensor current Ix is measured. The impedance of the sensor is determined as $$Rx=(Rcal)(Ical/Ib_1)(Ib_2/Ix),$$

where $Ib_1$ is the current in the bridge resistance when the excitation is $Vexc_1$ and $Ib_2$ is the current in the bridge resistance when the excitation is $Vexc_2$. Because the measurement excitation voltage and gain are the same for each pair of currents measurements, the accuracy of the measurement voltage and the gain in the measurement system is unimportant.

In an example intended to be illustrative and non-limiting, if the sensor impedance is known to be in the range of about 200Ω, and Rcal is 10 kΩ, the bridge resistance can be 1.128 kΩ. In this case the ratio of the bridge resistance and the calibration resistance, and the ratio of the bridge resistance and the sensor impedance may not be too large, and one value of bridge resistance can be used. The measurement circuit may apply an excitation signal to the sensor to get an estimate of the impedance before setting the value of the bridge resistance. The measurement is an estimate because the excitation signal typically doesn't have the required accuracy. The measurement circuit 616 may set the bridge resistance value to a coarse or approximate resistance value prior to more accurately determining the bridge resistance value. The measurement circuit 616 can also be used to measure the resistance of Rcal if desired. The multiplexer circuit 630 can be used to apply the excitation signal to the calibration resistance and the measurement circuit 616 can calculate the calibration resistance using the excitation signal.

In another example, if the impedance difference between the sensor impedance Rx and the calibration resistance Rcal is too large, multiple bridge resistance steps can be used to bridge the measurements between Rcal and Rx. For instance, the measurement circuit 616 may apply a first excitation signal $Vexc_1$ to the calibration and the first bridge resistance $Rb_1$ to measure the calibration current Ical and the first bridge current $Ib_{11}$ as in the previous example, where $Ib_{11}$ is the bridge current for the first bridge resistance value and the first excitation signal. The first bridge resistance value may be set closer to Rcal than Rx. The measurement circuit 616 applies a second excitation signal to the first bridge resistance value and a second bridge current $Ib_{12}$ is measured, where $Ib_{12}$ is the bridge current for the first bridge resistance value $Rb_1$ and the second excitation signal $Vexc_2$.

The bridge resistance is then changed to a second value $Rb_2$ that may be closer to Rx than Rcal. In an example intended to be illustrative and non-limiting, if the sensor impedance is known to be in the range of about 200Ω, and Rcal is 10 kΩ, the value of $Rb_1$ may be set to 712Ω and $Rb_2$ may be 2.53 kΩ. The second excitation signal $Vexc_2$ is applied to the second bridge resistance and a third bridge current $Ib_{22}$ is measured. A third excitation signal $Vexc_3$ is applied to the second bridge resistance $Rb_2$ and a fourth bridge current $Ib_{23}$ is measured, where $Ib_{23}$ is the bridge current for the second bridge resistance value $Rb_2$ and the third excitation signal $Vexc_3$. The third excitation signal is then applied to the sensor impedance Rx and the sensor current Ix is measured. The impedance of the sensor Rx can then be determined using the calibration resistance Rcal, the calibration current Ical, the first bridge current $Ib_{11}$, the second bridge current $Ib_{12}$, the third bridge current $Ib_{22}$, the fourth bridge current $Ib_{23}$, and the sensor current Ix, by $$Rx=(Rcal)(Ical/Ib_{11})(Ib_{12}/Ib_{22})(Ib_{23}/Ix).$$

Figure 7:
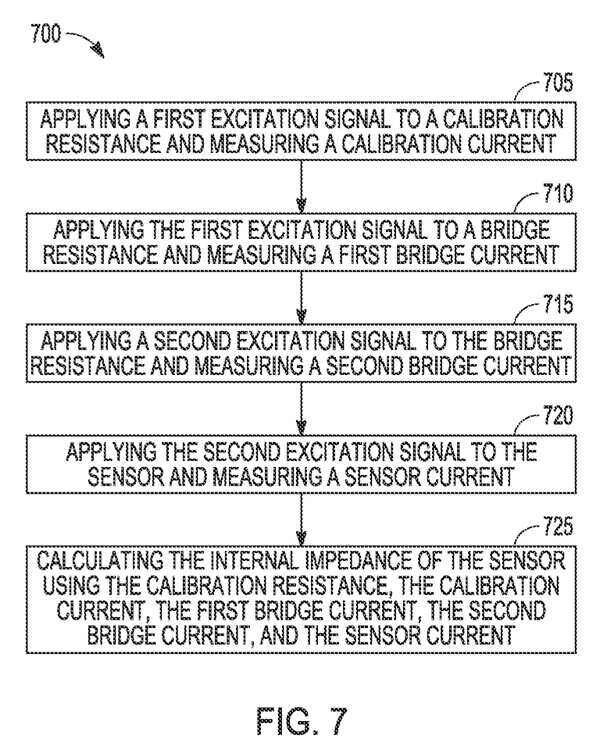
FIG. 7 is a flow diagram of an example of a method of controlling a test circuit to measure an internal impedance of an electronic sensor.

FIG. 7 is a flow diagram of an example of a method 700 of controlling a test circuit to measure an internal impedance of an electronic sensor. At 705, a first predetermined excitation signal is applied to a calibration resistance and a calibration current is measured. A bridge resistance value is then selected. In some examples, an approximate or coarse value of the sensor impedance is determined by the test circuit and the bridge resistance value is set accordingly by the test circuit or a user. The test circuit may include a table stored in memory, and the test circuit may set the bridge resistance by using the approximate sensor impedance as an index into the table. At 710, the same first excitation signal is applied to the bridge resistance and a first bridge current is measured.

At 715, a second predetermined excitation signal is applied to the bridge resistance and a second bridge current is measured. At 720, the same second excitation signal is applied to the sensor and a sensor current is measured. At 725, the internal impedance of the sensor is calculated by the test circuit using the calibration resistance, the calibration current, the first bridge current, the second bridge current, and the sensor current. The calculated impedance may then be to a user or process. For example, the internal impedance may be used to gauge the remaining useful life of the electronic sensor.

More than one bridge resistance may be needed. The bridge resistance may be determined according to a ratio. The test circuit may determine the bridge resistance to keep a ratio of the calibration impedance and the bridge impedance to about four. If the ratio of the selected bridge impedance and the approximate sensor value is not also within a desired ratio, the test circuit may select a second bridge resistance that is within the desired ratio of the sensor and within a desired ratio of the first bridge resistance value. The sensor impedance is then determined using the calibration resistance, the calibration current, four bridge currents and the sensor current as in the example described previously. This approach can be extended. More than two bridge resistances may be needed if the difference in values of the calibration resistance and the sensor impedance is too great.

Figure 8:
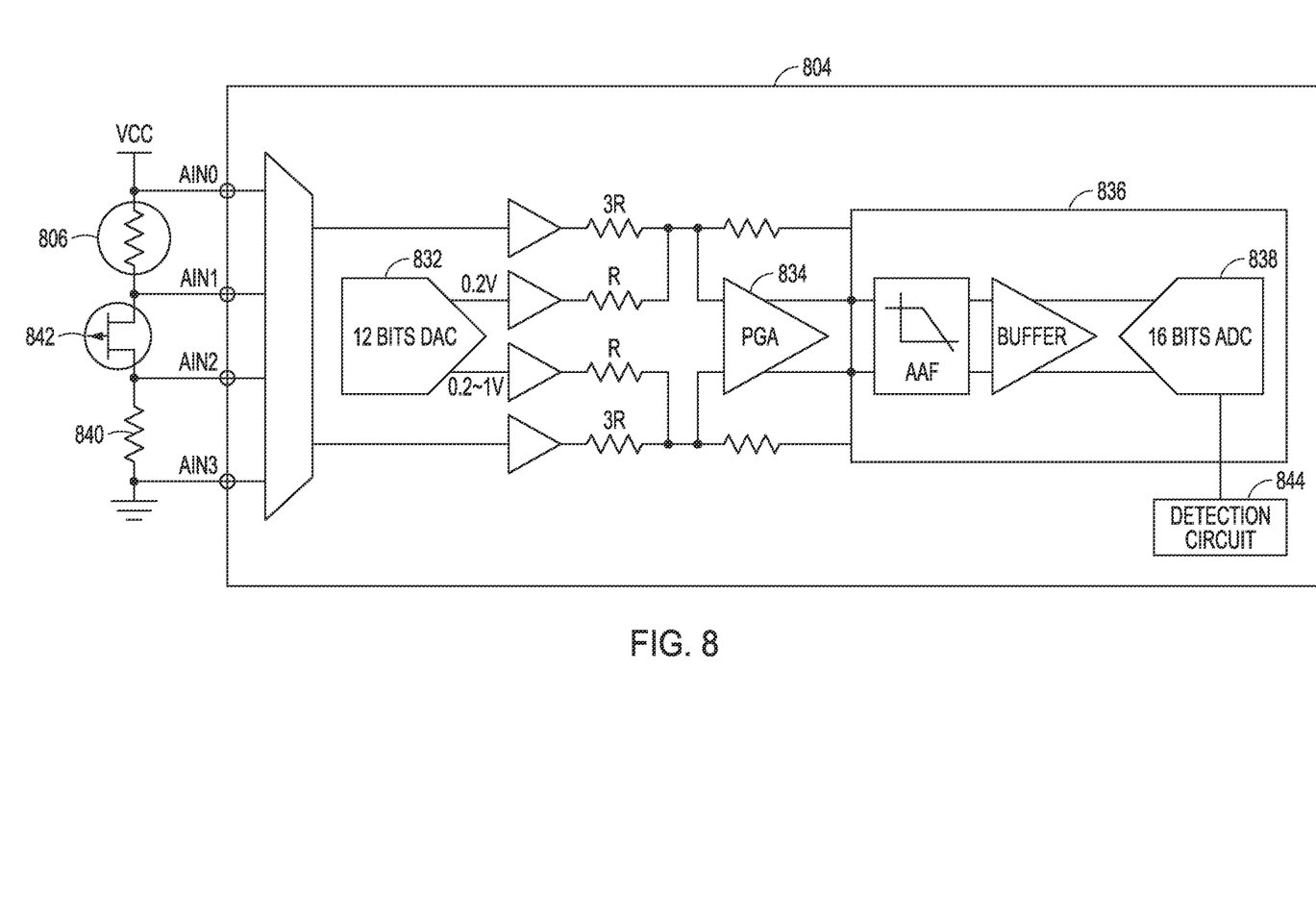
FIG. 8 is a circuit diagram of portions of another example of a test circuit electrically coupled to a sensor circuit.

FIG. 8 is a circuit diagram of portions of another example of a test circuit 804 electrically coupled to a sensor circuit 806. In addition to addressing power consumption and circuit noise, circuits to monitor the output of electronic sensors may need to tailor the output of the sensor circuits to improve accuracy.

The test circuit 804 can be included on an integrated circuit and includes an input to receive an electrical signal from the sensor circuit 806, a DAC circuit 832, a PGA 834, and measurement circuit 836. In certain examples, the sensor circuit is included on the same integrated circuit and the test circuit. The sensor can be used to detect a concentration of a chemical or gas within the environment containing the sensor. The internal impedance of the sensor varies with the concentration. The sensor is coupled to a resistive divider that includes a reference resistor 840 (Rref). A switch 842 may enable the resistive divider during measurement of the sensor output. The switch may also be activated for a short time (e.g., 200 microseconds (200 μs) to enable the current path through the sensor to briefly heat the sensor and then deactivated to save the power. By measuring Rref, the current can be monitored to precisely control the average power burning on the sensor, to precisely control the temperature to precisely control the sensitivity of the sensor for the measurement.

The measurement circuit 836 may include a controller to open the switch to conserve energy when a measurement is not performed. The voltage Vcc applied to the sensor is divided by the internal impedance of the sensor 806 and the reference resistor 840. To monitor the sensor, the voltage of the signal from the sensor varies with the concentration of the chemical or gas. For instance, the sensor may be a gas sensor. The internal impedance of the sensor may vary with the gas concentration and provide a voltage proportional to a concentration of the gas.

The signal from the sensor circuit 806 includes a direct current (DC) offset and a varying signal component. The DC offset can occur when the internal impedance of the sensor circuit has an approximate impedance that varies by a small amount. For example, the internal impedance of the sensor may vary from between 18Ω-20Ω over the range of the concentration of the gas. The voltage due to the 18Ω would appear as a DC offset in the electrical signal from the sensor.

Figure 9:
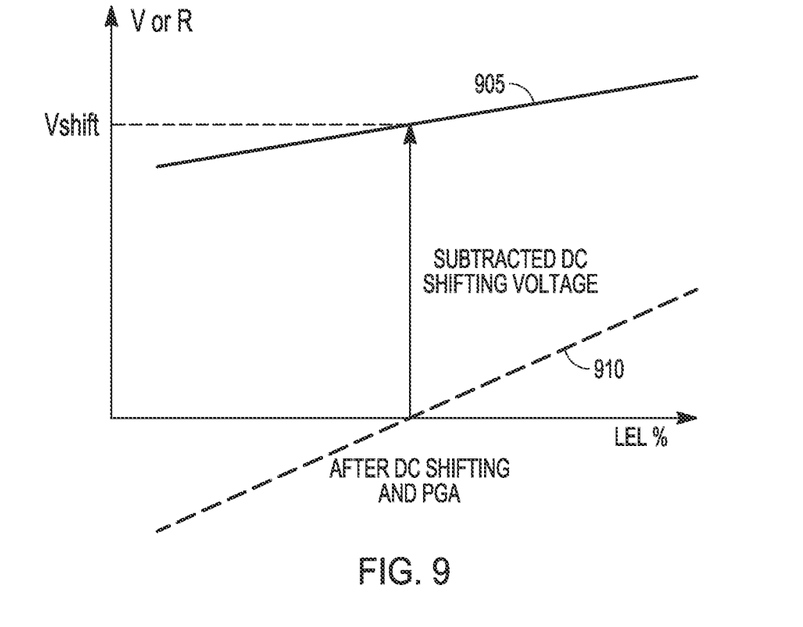
FIG. 9 is an example of the output of a sensor circuit.

FIG. 9 are graphs of an example of the output of the sensor circuit 806 as a function of the concentration of a gas. The DC component is shown as Vshift. Graph 905 shows that the voltage output varies between 2.37 Volts (2.37V) and 2.5V. The DC offset prevents using a lower voltage measurement circuit if desired and can limit the measurable range of the change in the output, which can impact accuracy of the measurement. To improve accuracy, the DC offset is removed. Graph 910 shows the output of the sensor after shifting the output to be centered on zero volts and signal gain applied to the signal from the sensor. The graph 910 shows that the accuracy of the measurement can be improved by the larger signal range, and a measurement circuit with a lower voltage can be used to monitor the output.

The test circuit 804 includes a DAC circuit 832 to remove the DC offset in the signal received from the sensor. The DAC circuit 832 can be programmed be user to subtract a known DC offset or automatically adjusted by a control circuit to subtract a measured DC offset. The PGA 834 applies signal gain to the signal shifted by the DAC circuit. The amount of gain provided by the PGA 834 may also be set by a user or automatically adjusted using a control circuit. The measurement circuit 836 generates a measure of the varying signal component. In some embodiments, the measurement circuit 836 includes an analog-to-digital converter (ADC) circuit 838 to generate a digital value representative of the signal form the sensor circuit 806. In the example of FIG. 8, the ADC circuit is a sixteen bit ADC circuit. The signal gain provided by the PGA allows for more signal swing that makes the accuracy of the 16-bit ADC more useful. Depending on the application, the measurement circuit may also include a fast Fourier transform (FFT) circuit configured to measure a frequency response of the varying signal component.

Figure 10:
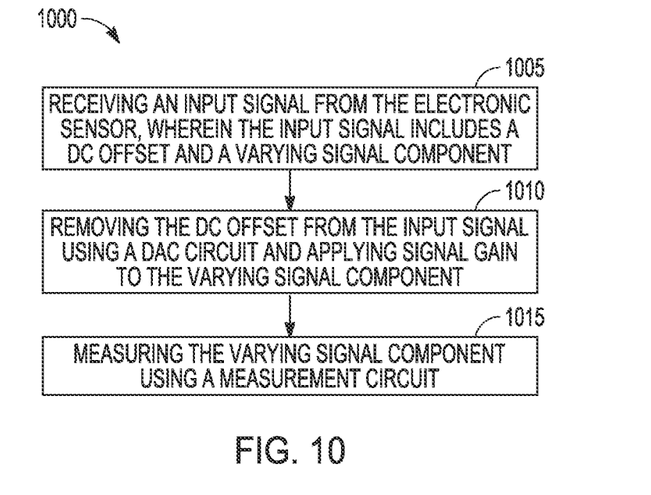
FIG. 10 is a flow diagram of an example of a method of controlling a test circuit to measure an internal impedance of an electronic sensor.

FIG. 10 is a flow diagram of an example of a method 1000 of controlling a test circuit to measure an internal impedance of an electronic sensor. At 1005, an input signal is received by the test circuit from the electronic sensor. The input signal includes a DC offset component and a varying signal component. At 1010, the DC offset is removed from the input signal using a DAC circuit and signal gain is applied to the remaining the varying signal component. At 1015, the varying signal component with the applied signal gain is measured using a measurement circuit. The measure can include a digital value determined using an ADC circuit. The measurement can be provided to one or both of a user or process. For instance, the sensor may be an oxygen sensor. As shown in FIG. 8, the test circuit can include a detection circuit 844. The detection circuit may generate an indication of a lower explosive limit (LEL) according to the measure of the varying signal component. The indication may be used to generate an alert regarding the LEL.

The devices, methods, and systems described herein allow for monitoring smart sensors with low power consumption, improved accuracy.

Additional Description

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects. Method examples described herein can be machine or computer-implemented at least in part.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising an integrated circuit, the integrated circuit including:
   an input to receive an electrical input signal from an electronic sensor, wherein the input signal includes a direct current (DC) offset and a varying signal component;
   a digital-to-analog converter (DAC) circuit configured to subtract the DC offset from the input signal;
   a programmable gain amplifier (PGA) operatively coupled to the DAC circuit, wherein the PGA circuit is configured to apply signal gain to the varying signal component of the input signal; and
   a measurement circuit configured to generate a measure of the varying signal component.

2. The apparatus of claim 1, wherein the measurement circuit includes an analog-to-digital converter (ADC) circuit configured to generate a measure of the varying signal component.

3. The apparatus of claim 1, wherein the measurement circuit includes a fast Fourier transform (FFT) circuit configured to measure a frequency response of the varying signal component.

4. The apparatus of claim 1, including the electronic sensor operatively coupled to the integrated circuit, wherein the electronic sensor is a resistive electronic sensor.

5. The apparatus of claim 4, wherein the electronic sensor is a gas sensor and the electrical signal from the electronic sensor is proportional to an amount of gas in an atmosphere.

6. The apparatus of claim 4, including a detection circuit, wherein the electronic sensor is an oxygen sensor, and the detection circuit is configured to generate an indication of a lower explosive limit according to the measure of the varying signal component.

7. The apparatus of claim 1, including:
a reference resistor connectable in series with the electronic sensor; and
wherein the measurement circuit is configured to connect the reference resistor to the electronic sensor when receiving the input signal from the electronic sensor.

8. The apparatus of claim 7, including:
a switch circuit connected to the reference resistor; and
wherein the measurement circuit is configured to activate the switch to connect the reference resistor to the electronic sensor when receiving the input signal from the electronic sensor and disconnect the resistor from the electronic sensor when not receiving input signal.

9. The apparatus of claim 1, wherein the DAC circuit is configured to center the varying signal component at zero volts and the PGA is configured to apply signal gain to the varying signal component centered at zero volts.

10. The apparatus of claim 9, including a sixteen bit analog-to-digital converter (ADC) circuit configured to generate sixteen bit digital values representative of the varying signal component centered at zero volts.

11. A method of monitoring an electronic sensor using a test circuit, the method comprising:
receiving an electrical input signal from the electronic sensor wherein the input signal includes a direct current (DC) offset and a varying signal component;
removing the DC offset from the input signal using a digital-to-analog converter (DAC) circuit of the test circuit;
applying signal gain to the remaining varying signal component using a programmable gain amplifier (PGA) operatively coupled to the DAC circuit; and
measuring the varying signal component with the applied signal gain.

12. The method of claim 11, wherein the measuring the varying signal component includes producing a digital value of the varying signal component using an analog-to-digital converter (ADC) circuit.

13. The method of claim 11, wherein the measuring the varying signal component includes measuring the frequency response of the varying signal component.

14. The method of claim 11, wherein the receiving the electrical input signal includes receiving the electrical input signal from a resistive electronic sensor.

15. The method of claim 11, wherein the receiving the electrical input signal includes receiving an electrical input signal that is proportional to an amount of gas in an atmosphere.

16. The method of claim 11,
wherein the receiving the electrical input signal includes receiving the electrical input signal from an oxygen sensor, and
measuring the varying signal component includes generating an indication of a lower explosive limit (LEL) according to the measure of the varying signal component.

17. The method of claim 11, including connecting a reference resistor to the electronic sensor when receiving the input signal from the electronic sensor.

18. The method of claim 17, including:
activating a switch of the test circuit to connect the reference resistor to the electronic sensor when receiving the input signal from the electronic sensor; and
deactivating the switch to disconnect the resistor from the electronic sensor when not receiving input signal.

19. The method of claim 11,
wherein the removing the DC offset from the input signal includes centering the remaining varying signal component at zero volts; and
wherein the applying the signal gain includes applying the signal gain to the varying signal component centered at zero volts.

20. The method of claim 19, wherein the measuring the varying signal component includes generating sixteen bit digital values representative of the varying signal component centered at zero volts.

* * * * *